United States Patent [19]

Lang et al.

[11] 4,364,490

[45] Dec. 21, 1982

[54] REFUSE RECEPTACLE WITH BAG LINERS SUPPLIED THROUGH THE BOTTOM FROM REPLACEABLE LINER SUPPLY PACKAGES

[75] Inventors: John Lang, Pinole; R. Scott Hunter, San Rafael, both of Calif.

[73] Assignee: Eric Reiner, Hollywood, Calif.

[21] Appl. No.: 155,669

[22] Filed: Jun. 2, 1980

[51] Int. Cl.³ .............................................. B65B 67/04
[52] U.S. Cl. ................................... 220/407; 220/404; 248/95; 206/390
[58] Field of Search ............... 206/390, 395, 408, 554; 221/33, 45, 46, 49, 61, 62, 70; 248/95, 97–101; 232/43.2; 312/35, 38, 41, 73, 91, 97.1; 220/404, 407, 461, 462

[56] References Cited

U.S. PATENT DOCUMENTS

| | | | |
|---|---|---|---|
| 2,117,689 | 5/1938 | Tatsch | 248/101 |
| 2,722,993 | 11/1955 | Gerber et al. | |
| 2,942,823 | 6/1960 | Chapman | 248/97 |
| 3,300,082 | 1/1967 | Patterson | 220/407 |
| 3,313,504 | 4/1967 | Stoltze | 248/99 |
| 3,358,823 | 12/1967 | Paxton | 206/390 |
| 3,392,825 | 7/1968 | Gale et al. | 220/407 X |
| 3,421,689 | 1/1969 | Reinzan | 232/43.2 |
| 3,451,453 | 6/1969 | Heck | 220/407 X |
| 3,476,341 | 11/1969 | Patterson | 248/95 |
| 3,481,112 | 12/1969 | Bourgeois | 220/407 X |
| 3,530,980 | 9/1970 | Link | 206/408 X |
| 3,552,697 | 1/1971 | Pinto | 248/97 |
| 3,760,975 | 9/1973 | Nilsson | 248/100 X |
| 3,800,503 | 4/1974 | Maki | 220/407 X |
| 3,958,768 | 5/1976 | Fairbanks | 206/390 X |

FOREIGN PATENT DOCUMENTS 1437228  3/1966  France .................................. 248/95

Primary Examiner—William Price
Assistant Examiner—Gary E. Elkins
Attorney, Agent, or Firm—Majestic, Gallagher, Parsons & Siebert

[57] ABSTRACT

A refuse receptacle with refuse bags being supplied from the bottom thereof from a replaceable package of said bags. The container has a general usefulness but is particularly adapted for use in counting and disposing of sponges and other articles during a surgical procedure.

20 Claims, 6 Drawing Figures

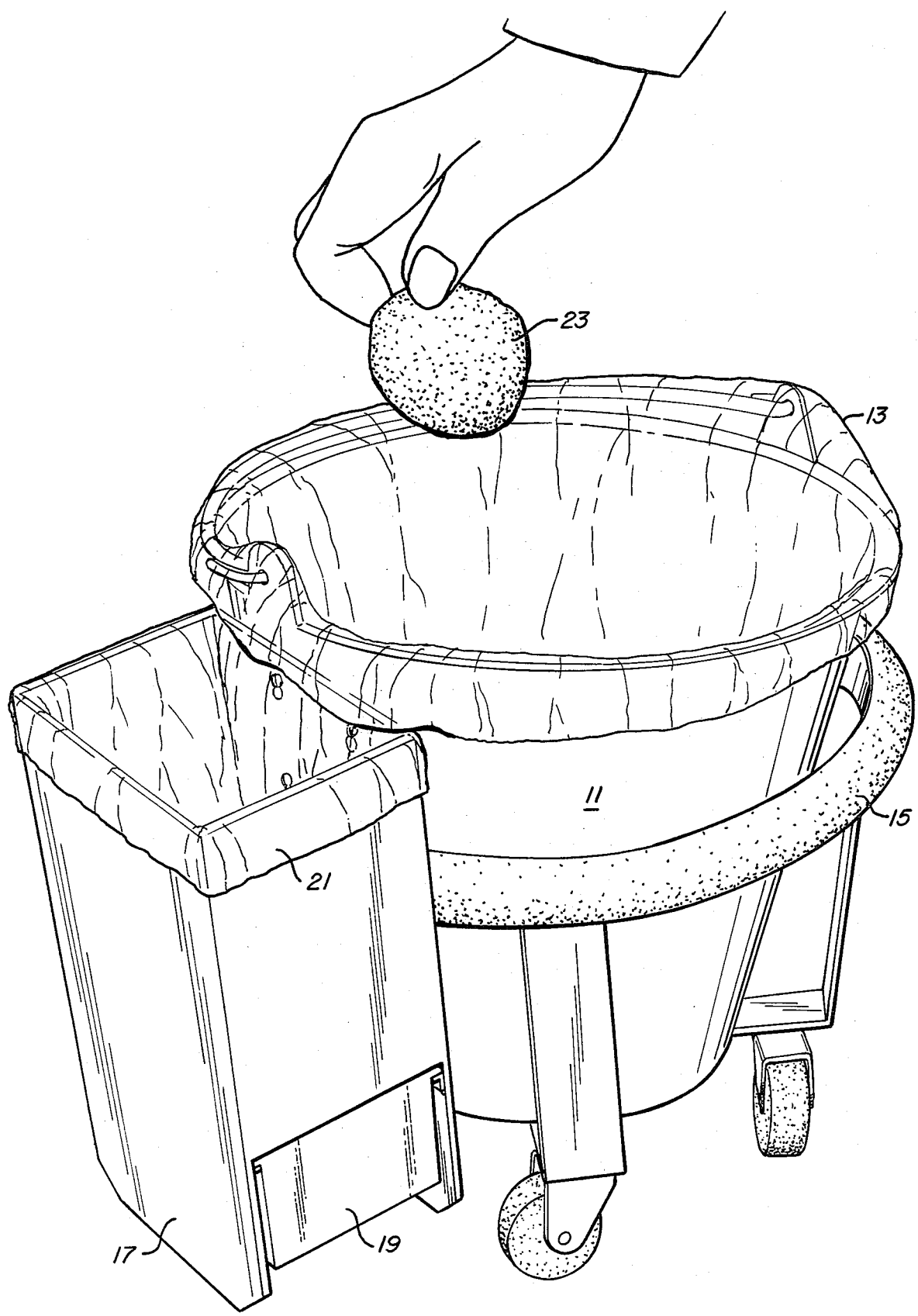
FIG._1A.

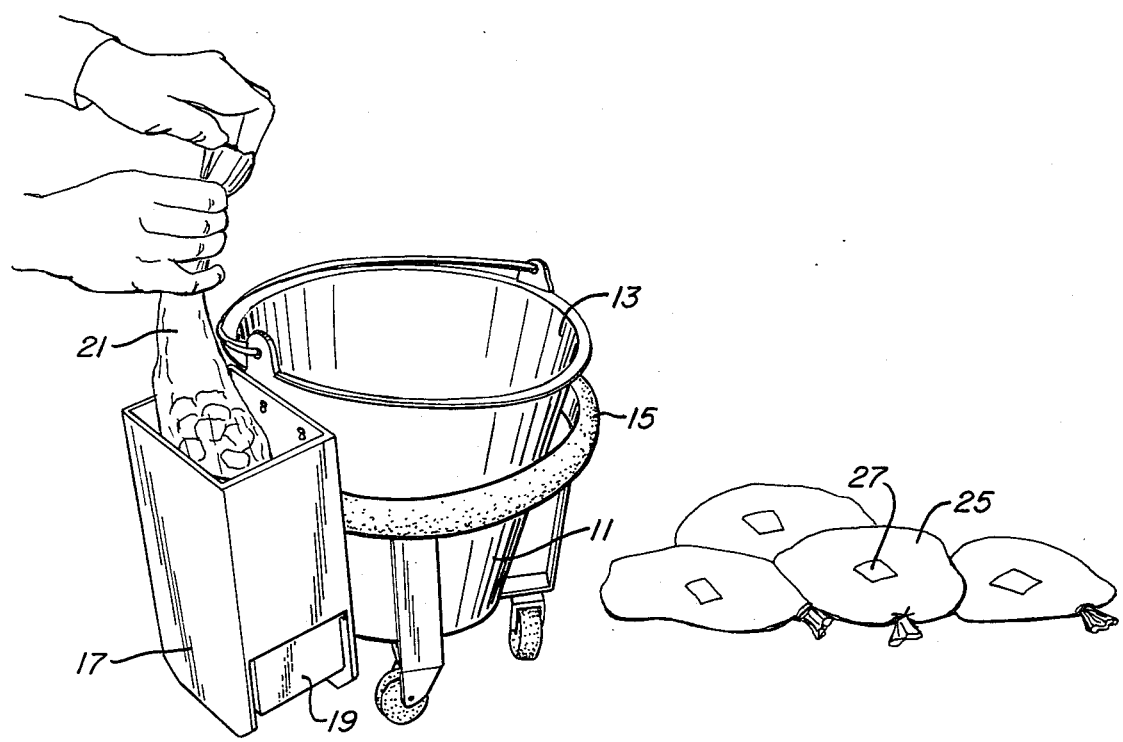
FIG._1B.

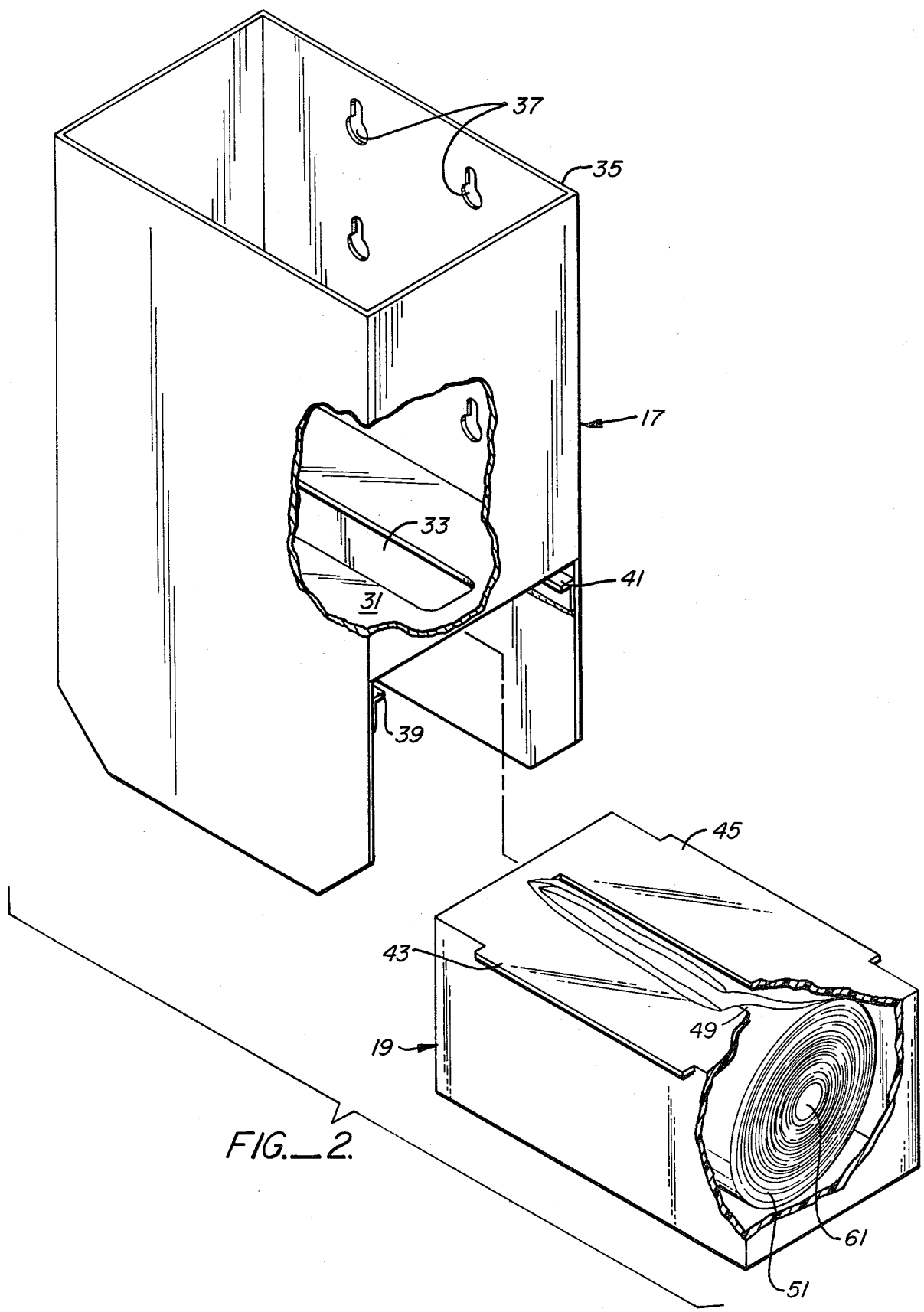
FIG._2.

U.S. Patent  Dec. 21, 1982  Sheet 4 of 4  4,364,490
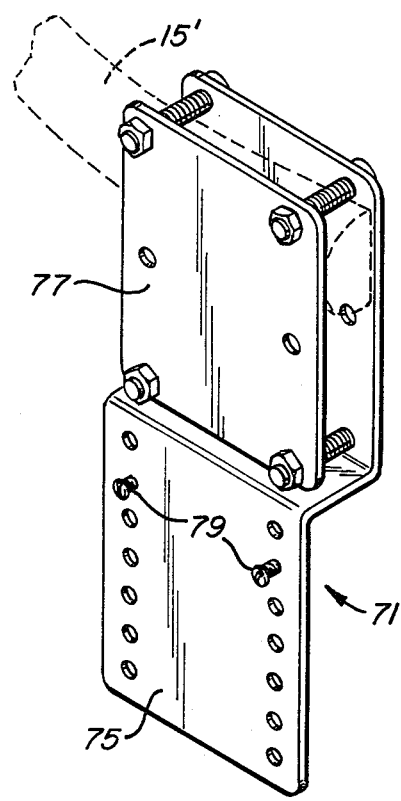
FIG._3A.
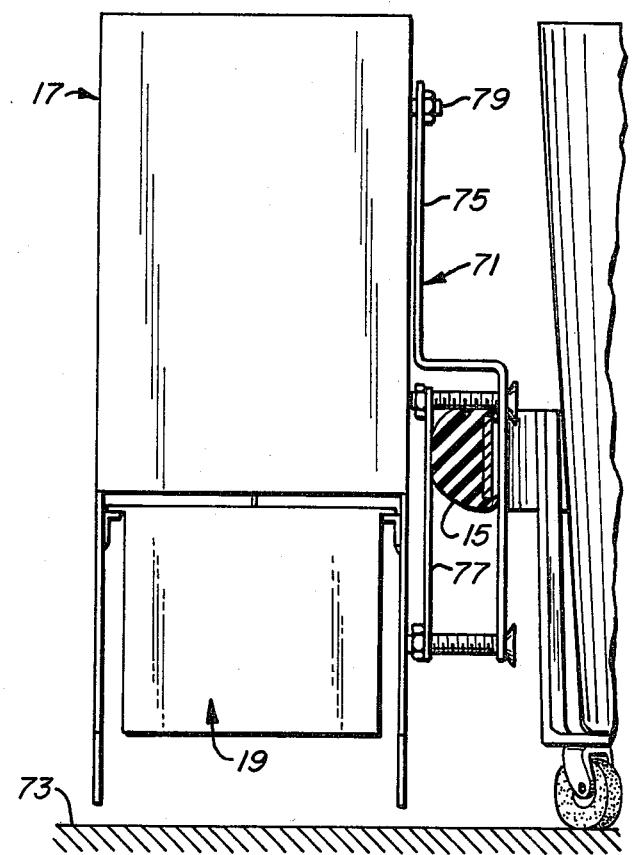
FIG._3B.
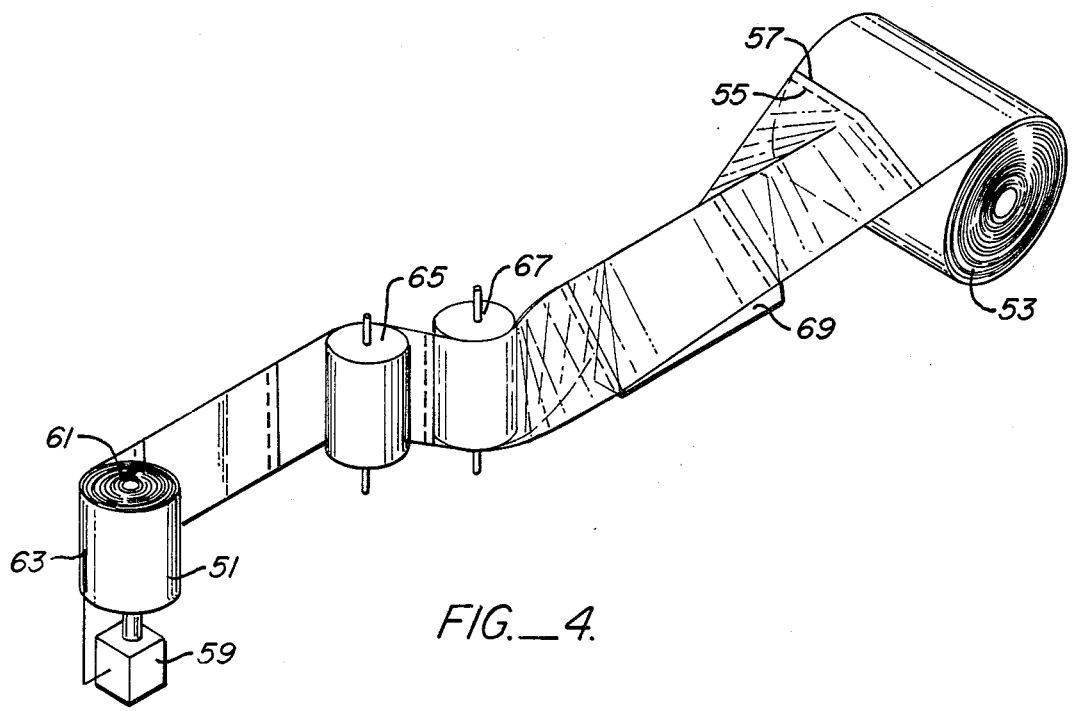
FIG._4.

REFUSE RECEPTACLE WITH BAG LINERS SUPPLIED THROUGH THE BOTTOM FROM REPLACEABLE LINER SUPPLY PACKAGES

BACKGROUND OF THE INVENTION

This invention relates generally to refuse receptacles and disposable liners therefor, particularly a receptacle and liner combination that is especially adapted for counting and disposing of sponges and other articles during a surgical procedure.

An important part of every human surgery is to ensure that all sponges, surgical instruments and the like are accounted for before the patient is sewn up. A predominant technique presently utilized for keeping track of sponges used in the surgery is to spread the used sponges on a disposable cover placed on the floor. The sponges are so placed as they are removed from a patient while undergoing surgery. When all of the sponges initially brought into the surgery room have been accounted for by so counting them, the surgery is then terminated by sewing up the patient, and the sponges are discarded after wrapping them up in the disposable floor cover.

Such existing surgical techniques are slow, cumbersome and require a great deal of space. Therefore, it is a primary object of the present invention to provide an article and technique of counting and disposing of the sponges that overcome these disadvantages.

It is another object of the present invention to provide a refuse container and replenishable refuse bag therefor which have general utility and which are economical, convenient, and of small size.

SUMMARY OF THE INVENTION

These and other objects are accomplished by the various aspects of the present invention, wherein, stated briefly, the used surgical sponges are packaged in disposable bags containing a certain number of sponges, such as five or ten. The bags themselves can then be spread out and a count of the total number of sponges made very quickly. A refuse receptacle is provided for being lined by such plastic disposable bags which are fed into the receptacle from a slot in its bottom refuse bag supporting structure. Replenishable packages of bags are provided with outwardly extending flanges that cooperate with tracks installed in the receptacle a small distance below the receptacle lower support surface. The package of bags has a slot in the top surface thereof which automatically aligns with the slot in the bottom support surface of the receptacle, so that the bags may be withdrawn into the receptacle through its bottom slot. The bags contained in the replenishable package are folded over across their width, so that when opened for lining the interior of the receptacle the entire receptacle is covered even though the width of the folded bag within the package is less than one dimension of the receptacle.

Other objects, advantages and features of the present invention will become apparent from the following description of its preferred embodiments which should be taken in conjunction with the accompanying drawings.

BRIEF DESCRIPTION OF THE DRAWINGS

FIGS. 1A and 1B illustrate the use of a refuse receptacle according to the present invention in disposing of surgical sponges;

FIG. 2 is an expanded view of the receptacle shown in FIGS. 1A and 1B;

FIGS. 3A and 3B show the use of a mounting bracket for the receptacle in the embodiments of FIGS. 1A and 1B; and FIG. 4 illustrates a technique and machine for packaging disposable bags.

DESCRIPTION OF THE PREFERRED EMBODIMENTS

Referring initially to FIGS. 1A and 1B, the surgical sponge application of the receptacle and replenishable package of refuse bags is shown generally. A bucket 11 is lined on its interior with a liner 13. The bucket is carried by a rail structure 15 which is provided with wheels to facilitate movement. The bucket and rail structures are made of stainless steel and are standard items of hospital operating rooms, although various shapes and sizes of such items are commercially available.

To these standard items is attached a receptacle 17 into which a package 19 is removably inserted. The package 19 contains a supply of disposable plastic bags for lining the interior of the receptacle. One such bag 21 is shown in place in FIG. 1A, being turned over and held by the upper edges of the side walls of the receptacle 17. The liners 21 are supplied from the package 19 through the bottom of the receptacle 17.

The items shown in FIGS. 1A and 1B are utilized, according to one aspect of the present invention, in a hospital operating room. Used sponges being removed from the patient operated on (such as sponge 23 of FIG. 1A) are initially deposited within the bucket 11 in the liner 13. Periodically, a certain number of such sponges are counted by the operating room nurse into the receptacle bag liner 21. For example, five sponges may be placed in each bag, in the case of large sponges, or ten smaller sponges may be placed in the bag 21. When the specified number are in the bag 21, it is pulled upward, as shown in FIG. 1B, and its open top closed. According to the example described herein, each of the bags, such as the bag 21, is provided in a continuous roll so that when the bag 21 is pulled upwards the next bag is automatically removed from the package 19. After the bag 21 is removed by tearing across its perforations that separate the bag 21 from the next connected bag, the open end of the next bag is folded over the top edges of the receptacle 17. When the bag 21 is so separated, it is added to a grouping of previously filled bags, such as the four bags shown in FIG. 1B.

These bags are made of clear, thin, flexible plastic. On each bag, such as the bag 25 of FIG. 1B, is provided a light opaque patch printed thereon, such as the patch 27, so that the number of sponges in that particular bag may be written on the bag by the operating room nurse with the use of an appropriate pen. It may be easiest to count and keep track of the sponges if each such bag has the same number, but due to the varying sizes of the sponges which may be used, different numbers may be placed in some bags with the numbers of sponges in each bag marked thereon. As the surgical procedure is completed, therefore, the number of sponges may more easily and rapidly be ascertained by adding the numbers written on each bag. When it has been determined that all of the sponges present at the beginning of the operation have been accounted for, the bags of sponges are discarded.

Referring to FIG. 2, the structure of the receptacle 17 and package 19 of disposable bags is illustrated. The receptacle 17 includes a bottom plate 31, in this example a solid plate except for a bag receiving slot 33. The crosssection of the receptacle 17 is, in this example, rectilinear in shape and uniform throughout the height of the receptacle from its base plate 31 to its top bag-holding edge 35. The slot 33 is centered across the narrow dimension of the bottom plate 31 and extends nearly its entire length. The sidewalls of the receptacle 17 are solid, except for a plurality of apertures 37 in a wide sidewall thereof, utilized for attaching the receptacle to a supporting structure, as described hereinafter. The sidewalls also extend downward below the bottom plate 31, except on one narrow side thereof which serves as an opening for inserting and removing a package 19 of disposable bags.

Beneath the bottom plate 31 are a pair of tracks 39 and 41 held by the wide sidewalls of the receptacle 17 in a manner to extend inward. The package 19 is constructed with cooperating flanges 43 and 45 on opposite sides thereof. The package 19 has a width slightly less than the space between the tracks 39 and 41, except for the flanges 43 and 45 which are adapted for riding on top of the rails 39 and 41. Thus, the package 19 can easily slide into the underside of the receptacle 17 to insert a new supply of disposable bags and be removed therefrom when the bags of a particular package have all been used. The flanges 43 and 45, as well as the top surface of the package 19 generally, are made sufficiently stiff to hold the weight of the package. No bottom supporting structure beneath the package need be provided in the receptacle 17. This eliminates a potential collector of dust, dirt, blood and other contaminants that would be difficult to clean.

The package top surface in addition has a slot therein for removal of the disposable bags carried thereby. The slot 49 is positioned so that when the package 19 is inserted into the receptacle 17 it is aligned with the slot 33 of the receptacle bottom plate 31. The tracks 39 and 41 of the receptacle, and the flanges 43 and 45 of the package, are provided parallel to their respective slots and extended the long dimension of their rectilinear shape. Of course, other shapes can be utilized, but the relative shapes shown are preferred.

A number of techniques are possible for packaging the bags within the container 19 so that when one bag is pulled out of the package another bag is readied in position for subsequent use. In the embodiment shown here, a roll 51 of such bags is provided with perforations used to enable separation of each bag one at a time from the roll 51. It will be appreciated that since the package 19 is no wider, and in fact somewhat smaller, than the long dimension of the receptacle 17, a flat bag having only that width will not be able to fill the rectilinear crosssectional area within the receptacle 17 when pulled up through the slot 33. According to another aspect of the present invention, in order to allow such expansion, bag material which is wide enough to completely fill the receptacle 17 is utilized but then folded across its width before being rolled up and placed within the package 19. The manner in which the bag is rolled can best be illustrated by a schematic of the process for doing so as shown in FIG. 4.

A bulk supply of bags 53 is divided among many packages by individually forming, one at a time, each roll, such as the roll 51 of the package 19. The bags in th roll 53 are of a standard type widely used in other applications such as in grocery stores produce bags for customers' use. The roll is a continuous length of tubular material provided with single folds on either side. Periodically along its length are provided adjacent perforations 55 and welds 57 that extend completely across the entire width of the tubular material. Each perforation and weld is situated adjacent one to another. It will be noted that the supply roll 53 is wound with the bottom of the bags coming off first, so that the resulting roll 51 has the opened end of the bags coming off first. Since commercially available rolls of bags are generally wound to have the opened end of the bag lead, an additional step, not shown, of rewinding the purchased roll into the roll 53 must be performed.

A motor 59 drives a cylindrical cardboard tube to which the bag material is attached. A sensor 63 automatically shuts off the motor 59 when the thickness of the roll 51 reaches a pre-determined thickness. Alternatively, any number of commercially available linear counters may be utilized. Rollers 65 and 67 pinch the material and guide it across a folding implement 69 positioned with its elongated edge substantially in the middle of the width of the material and oriented in the direction in which the material is being pulled.

As shown in FIG. 2, the resulting roll 51 of bags has four layers of thickness at any point across it. There are the two folded edges of the original material supplied by the roll 53 and also the center fold added during the procedure illustrated in FIG. 4. This allows the bag to be expanded into the larger volume within the receptacle 17 as it is pulled from the package 19. Of course, the bags need not be folded at exactly the half-way point between their edges, but rather may be overlapped less than that shown in FIGS. 2 and 4 and still provide a capability of expanding within the receptacle 17. However, folding half-way between the edges is the most convenient and easiest to control. This folding technique is easily accomplished without having complicated gussets as are often used in presently available packaging materials.

The package 19 is most conveniently made of a paper-based cardboard material. The bag roll 51 is simply placed in the container without any roll or other element connecting the roll 51 and package 19.

Although the combination of the receptacle 17 and package 19 illustrated with respect to FIGS. 2 and 4 have a specific advantageous application for counting surgical sponges, as illustrated with respect to FIGS. 1A and 1B, it will be recognized that the disposable material receptacle of FIG. 2 has numerous other applications as well. Potential uses in the home and other areas of a hospital are other examples. However, referring again to the medical applications of FIGS. 1A and 1B, a particular bracket 71 is shown in FIGS. 3A and 3B as being especially advantageous for mounting the receptacle 17 onto a commercially used rail 15. It is desired that the receptacle be mounted as close to the floor 73 as possible, so that if it becomes heavy enough to tip the rail 15, such tipping will be extremely slight. Since various commercially available rails are different distances from the floor, the bracket 71 enables the receptacle 17 to be mounted close to the floor on a wide variety of commercially available rails. Two bracket plates 75 and 77 are provided. To one end of the bracket 75 is connected by four screws, as shown in FIG. 3A, the second bracket 77. The distance between the bottom and top sets of screws is several times the height of most commercially available rails 15, so that it may be positioned vertically on the rail 15 at a desired position. Also, the bracket 71 may be positioned descending from a rail 15' as shown in FIG. 3A, or may be inverted, as shown in FIG. 3B, thus providing a wide range of elevations possible for holding the container 17. When properly positioned on the rail, the bracket 71 is caused to tightly grip the rail by pulling the plates together upon tightening the four screws shown.

The opposite end of the plate 75 is provided with two parallel rows of holes in which a pair of opposing screws 79 may be positioned at a desired location for a particular rail and receptacle to be mounted together. The screws 79 are sized to fit within rear plate keyshaped holes 37 at the larger bottom end portion. Several elevational positions of the holes 37 are provided on the receptacle 17, and thus make a very fine adjustment possible of the receptacle 17 position on a given rail, since the screws 79 may be positioned at a number of discreet vertical positions as well.

Although the various aspects of the present invention have been described with respect to the preferred embodiments thereof, it will be understood that the invention is entitled to protection within the full scope of the appended claims.

It is claimed:

1. For a disposable material receptacle adapted to be lined by disposable bags that are fed one at a time into the receptacle from its bottom, a package of such disposable bags, comprising:
a container having top and side surfaces, said top surface being flat and rectilinearly shaped with an elongated slot therein opening into the interior of said container, said top surface extending beyond side surfaces on opposite sides of said slot to form outwardly extending flanges parallel to the length of said elongated slot, said flanges being stiff enough to support the weight of said package beneath said receptacle; and
a continuous length of a plurality of bags carried in the form of a roll within said container in a manner to be freely rotatable therein as the length of bags is withdrawn therefrom through said top slot, said continuous length of bags being in the form of a length of tubular material that is periodically along its length both sealed and perforated thereacross adjacent one another, said material additionally being folded over itself across its width so that the roll has a width substantially less than the width of said material.

2. The package according to claim 1 wherein said continuous bag material is folded over itself so that the roll is approximately one-half the width of said material.

3. The package according to claim 1 wherein said container is made of cardboard and said bag material is a flexible plastic material.

4. The package according to claim 1 wherein said roll of bags is made of substantially transparent plastic with a light colored opaque area provided on the surface of each bag, whereby a notation concerning the nature of the contents of each bag may be made by a user of each bag.

5. The package according to claim 1 wherein said slot has an extent in its longest direction that is significantly less than the full unfolded width of said tubular material.

6. The package according to claim 1 wherein said roll is carried within said container without any attachment therewith.

7. For a disposable material receptacle adapted to be lined by disposable bags that are fed one at a time into the receptacle from its bottom, a package of such disposable bags, comprising:
a container having top and side sufaces, said top surface being flat and rectilinearly shaped with an elongated slot therein opening into the interior of said container, said top surface extending beyond side surfaces on opposite sides of said slot to form outwardly extending flanges parallel to the length of said elongated slot, said flanges being stiff enough to support the weight of said package beneath said receptacle; and
a plurality of bags carried within said container in a manner to continuously feed said bags of said slot one at a time in response to a bag being pulled out of said container through said slot.

8. The package according to claim 7 wherein each of said plurality of bags is folded over itself across its width in a manner that there are four layers of bag material at substantially all points across the width, whereby each bag expands upon withdrawal from the package for lining the full extent of said receptacle.

9. A refuse disposal system comprising:
a cartridge containing a plurality of refuse bags arranged therein to be removed one at a time through an opening therein, said bags having one end openable to receive refuse therein and another end closed, said bags being oriented in the cartridge for the bags' one end to be removed first through said opening,
a frame having means for holding upright and open said one bag end and means for supporting said another end in a manner to hold the weight of the bag when containing refuse therein, and
cooperative means carried by said frame and said cartridge for removably holding the cartridge therein in a position so that the bags are drawn therefrom into said frame at a location adjacent said another bag end supporting means, wherein said cooperative cartridge holding means includes flanges extending outward from opposite sides of said cartridge and mating slots provided on said frame adopted to receive said flanges, thereby holding the cartridge in place on said frame.

10. A refuse receptacle and cartridge of disposable refuse bags, comprising:
a frame adapted for holding upright and open a top opening of a refuse bag,
a lower support structure held fixed with respect to said frame, thereby to provide support for the bottom of a refuse bag,
a slot provided in said lower support structure for receiving a supply of refuse bags therethrough,
means positioned immediately beneath said lower support structure for removably holding said cartridge, said removable holding means comprising a pair of tracks on opposite sides of said lower support structure, thereby slidably receiving a supporting portion of said cartridge, and
said cartridge comprising a top surface with a slot therein through which refuse bags may be withdrawn one at a time, and a pair of flanges on opposite sides of said package at its top surface, said flanges being shaped and positioned to be received by the tracks of the receptacle, whereby the cartridge is removably held at the bottom of said receptacle, said cartridge top surface slot further being positioned to be aligned with the slot of said receptacle lower support structure, whereby refuse bags may be withdrawn from the cartridge through said receptacle slot.

11. A refuse receptacle, comprising:
a frame adapted for holding upright and open a top opening of a refuse bag;
a lower support structure held fixed with respect to said frame, thereby to provide support for the bottom of a refuse bag,
a slot provided in said lower support structure for receiving a supply of refuse bags therethrough,
means positioned immediately beneath said lower support structure for removably holding a cartridge of a plurality of refuse bags, said removable holding means comprising a pair of tracks on opposite sides of said lower support structure, thereby slidably receiving a supporting portion of said cartridge, and
said cartridge having flanges extending on opposite sides thereof with a position and shape for removable insertion into the receptacle in a manner to be held against gravity by said pair of tracks, said cartridge additionally including a slot in its top surface positioned for alignment with the slot of the receptacle lower support structure when the cartridge is so inserted therein, a plurality of refuse bags being carried by such cartridge and comprising a continuous length of a plurality of bags carried in the form of a roll therewithin in a manner to be freely rotatable as the length of said bag is withdrawn through said container slot, said continuous length of bags being in the form of a length of tubular material that is periodically along its length both sealed and perforated thereacross adjacent one another, said material additionally being folded over itself across its width so that the roll has a width substantially less than the width of said material.

12. The receptacle according to claim 10, wherein said lower support structure is a rectilinearly shaped plate with unequal side lengths and said slot being elongated in the direction of the long dimension of said bottom plate, said pair of tracks being held a distance beneath said plate and oriented on either side of said slot parallel to its long dimension.

13. The receptacle according to claim 12, wherein said frame has solid side walls, the top edges of said walls forming a rectilinear frame, said walls descending from said bottom plate as well along its two long sides and one short side, the space beneath said plate along one of its short sides remaining open to receive said cartridge.

14. The receptacle according to claim 10 which additionally comprises a bracket for adjustably attaching said receptacle to a rail, said bracket having a pair of compression plates in which said rail may be received at adjusted elevations therebetween.

15. The refuse receptacle according to claim 14 wherein said bracket additionally includes means cooperatively provided with respect to said receptacle for removable mounting said bracket thereon at a plurality of specific elevations along its height.

16. The receptacle according to claim 10, wherein said frame is open to the outside beneath said tracks.

17. The receptacle according to claim 11, wherein said lower support structure is a rectilinearly shaped plate with unequal side lengths and said slot being elongated in the direction of the long dimension of said bottom plate, said pair of tracks being held a distance beneath said plate and oriented on either side of said slot parallel to its long dimension.

18. The receptacle according to claim 17, wherein said frame has solid side walls, the top edges of said walls forming a rectilinear frame, said walls descending from said bottom plate as well along its two long sides and one short side, the space beneath said plate along one of its short sides remaining open to receive said cartridge.

19. The receptacle according to claim 11 which additionally comprises a bracket for adjustably attaching said receptacle to a rail, said bracket having a pair of compression plates in which said rail may be received at adjusted elevations therebetween.

20. The refuse receptacle according to claim 19 wherein said bracket additionally includes means cooperatively provided with respect to said receptacle for removable mounting said bracket thereon at a plurality of specific elevations along its height.

* * * * *